United States Patent [19]

McWhorter

[11] 4,391,128
[45] Jul. 5, 1983

[54] BACK-DIFFUSION QUALITY CONTROL METHOD FOR BARRIER TREATED CONTAINERS

[75] Inventor: Thomas E. McWhorter, Whitehall, Pa.

[73] Assignee: Air Products and Chemicals, Inc., Allentown, Pa.

[21] Appl. No.: 255,958

[22] Filed: Apr. 20, 1981

[51] Int. Cl.³ ............................................. G01N 15/08
[52] U.S. Cl. ......................................................... 73/38
[58] Field of Search ....................................... 73/38, 19

[56] References Cited

U.S. PATENT DOCUMENTS

| | | | |
|---|---|---|---|
| 2,811,468 | 10/1957 | Joffre | 117/95 |
| 3,301,043 | 1/1967 | Lyssy | 73/38 |
| 3,431,772 | 3/1969 | Sunner et al. | 73/38 |
| 3,498,110 | 3/1970 | Brun | 73/38 |
| 3,618,361 | 11/1971 | Stephens et al. | 73/38 |
| 3,862,284 | 5/1973 | Dixon et al. | 264/83 |
| 4,047,422 | 9/1977 | Lyssy | 73/38 |

OTHER PUBLICATIONS

A. J. Woytek and J. F. Gentilcore, Fluorination of Polyolefin Containers During Blow Molding to Reduce Solvent Permeation, Mar. 1979, pp. 10–16.

Industrial Blow Molding: The Sleeping Giant Stirs, Nov. 1977, pp. 34–37.

Blow Molding: *The Next Five Years*, in Plastics Technology, Jun. 1979, pp. 61–64.

*Primary Examiner*—E. R. Kazenske
*Assistant Examiner*—Joseph W. Roskos
*Attorney, Agent, or Firm*—Mark L. Rodgers; E. Eugene Innis; J. C. Simmons

[57] ABSTRACT

A process is provided for making a distinction between solid, porous materials, e.g. thermoplastics, having surfaces which are either untreated or treated to render them measurably impermeable to volatiles. The surfaces are first exposed to a high concentration of a volatile fluid which is removed after a fixed time period. The surfaces are then exposed to an environment, e.g. a vacuum, to cause the volatile fluid to back-diffuse and the fluid that back-diffuses is measured. The rate at which the fluid back-diffuses from the untreated surface is considerably greater than that of the treated surface.

10 Claims, 1 Drawing Figure

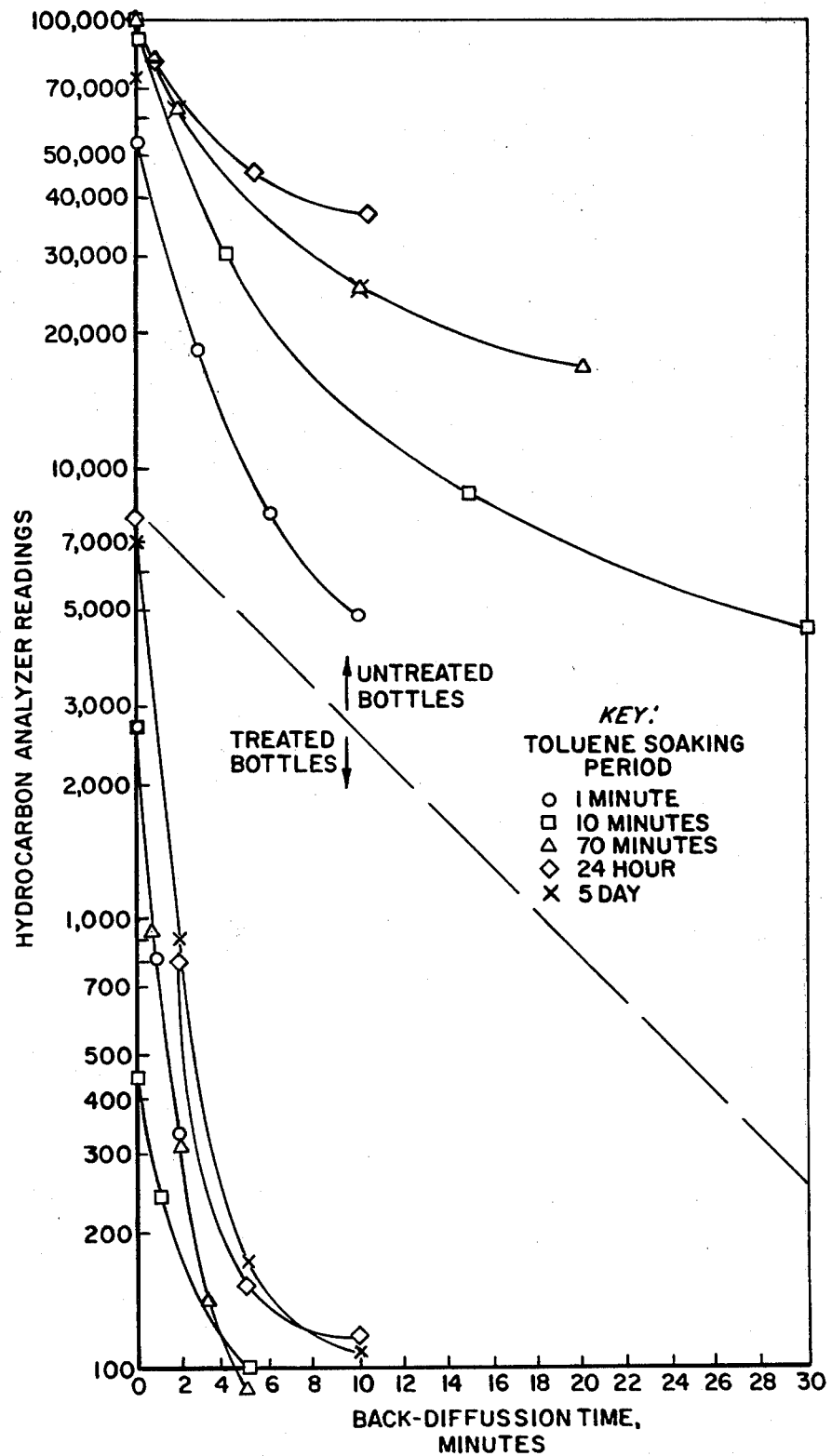

BACK-DIFFUSION QUALITY CONTROL METHOD FOR BARRIER TREATED CONTAINERS

TECHNICAL FIELD

This invention relates to a quality control method for determining the degree of impermeability of barrier treated solid materials to volatile substances. In particular, it relates to a method for determining whether containers and other articles have been treated to impart a measurable impermeability to hydrocarbons.

BACKGROUND OF THE PRIOR ART

The use of blow molded thermoplastic containers and other hollow articles for a wide variety of liquids has gained wide spread commercial importance; see the article entitled "Blow Molding: The Next Five Years" in Plastics Technology, June 1979, pages 61–64. Blow molding permits the fabrication of lightweight, intricately shaped containers which are corrosion-resistant and mechanically strong. For many applications, such as the storage of aqueous or other highly polar liquids, these containers are, for all practical purposes, impervious to the contained substances. In other applications, however, where relatively nonpolar volatile organic fluids are to be held, blow molded containers have little if any value because of the ability of such volatile substances to diffuse through the walls of the thermoplastic containers. Nonpolar substances which are presently of greatest commercial interest as contained liquids include gasoline and other liquid fuels, hydrocarbon-based cleaning fluids and other household solvents, and oil-based paints containing volatile hydrocarbons. Diffusion of such fluids often results in an unacceptable loss of at least a part of the constituents making up the contained liquids. In the case of oil-based paints, the more volatile substances are lost by diffusion and the properties of the paint dramatically change to make it of little value.

Examples of thermoplastic materials or resins which have been employed in the production of blow molded articles include polymers and copolymers of styrene, acrylonitrile, vinyl chloride and olefins having at least one aliphatic mono-1-olefin with a maximum of 8 carbon atoms per molecule and PET (polyethylene terphthalate). The preferred types of thermoplastic materials for blow molding include polyolefins and copolymers of ethylene, propylene, 1-butene, 1-pentene, 4-methyl-1-pentene, 3-methyl-1-butene and 3,3-dimethyl-1-butene.

An additional problem with the containment of volatile nonpolar fluids in thermoplastic containers is the possibility that the concentration of flammable substances in the environment outside the container can reach a level to create an extremely explosive atmosphere.

In an attempt to overcome the direct diffusion of the volatiles through the walls of blow molded thermoplastic containers, a number of processes have been commercialized for treating their surfaces either during or after the blow molding process.

A post-treating method for providing a barrier coating and rendering the blow molded polyolefin bottles relatively impermeable to the passage of nonpolar solvents is described in U.S. Pat. No. 2,811,468. In this process, the surface of the previously formed blow molded bottle is fluorinated with pure fluorine or a mixture of fluorine and air or nitrogen. The resulting fluorinated containers have been found to be greatly improved in their barrier properties with respect to hydrocarbon solvents.

A more efficient and economical process for obtaining containers having improved barrier properties is described in U.S. Pat. No. 3,862,284, assigned to Air Products and Chemicals, Inc., the assignee of the present application, which process comprises blending 0.1 to 10% by volume fluorine and 99.9 to 90% by volume inert gas into a fluid medium prior to expanding the parison within the closed mold to conform the parison to the contour of the mold. The containers produced by this process, which has been designated as the AIRO-PAK Process, have an interior surface which possesses extremely high resistance to permeation by organic molecules; see the article entitled "Fluorination of Polyolefin Container, During Blow Moulding to Reduce Solvent Permeation" in Plastics and Rubber Processing, March 1979, pages 10–16.

Another commercially available process for improving the barrier properties of blow molded containers involves post-treating the container with a gaseous mixture of sulfur trioxide, ammonia and a dry diluent gas, which is known as the Dow sulfonation process; see the article entitled "Industrial Blow Molding: The Sleeping Giant Stirs" in Modern Plastics, November 1977, pages 34–37, at page 37.

The manufacture of barrier coated thermoplastic containers by any of the commercially available methods is hampered by the lack of a rapid, inexpensive quality control method to determine the effectiveness of the inner surface treatment in minimizing solvent loss by permeation through the walls of the container. One method is simply to directly measure the loss in weight of a container filled with the solvent over a period of time. However, this method requires days or even weeks in order to obtain a significant measurable loss of solvent through the walls of the container by direct diffusion. Obviously such a test is impractical for use as a production quality control method where it is essential to dectet any processing difficulties as soon as they occur so that immediate corrective action can be taken.

A number of quality control methods have been used to provide more rapid means for determining the impermeability of a container, such methods fall into two broad classes. The direct methods measure the permeability of the solvent through the walls of container. Indirect methods depend upon a measurement of characteristics other than permeability of the container, but which relate to permeability. The chief disadvantage of many of these prior art methods is that they result in the destruction of the container and a loss of production. Such losses can be very significant in the quality control of large blow molded containers such as 55 gallon high density polyethylene (HDPE) drums and HDPE gasoline tanks.

One direct method that is used is the pressure-accelerated permeability measurement method in which a sample is cut out of a container and mounted in a high pressure test cell. A liquid or gas is forced to diffuse under high pressure through the wall of the sample to the other side where its presence is detected either by chemical or physical means. In addition to the disadvantage of being one of the destructive quality control tests, it still may require hours or days to determine the permeability of a given sample.

Another direct method for permeability measurement is the dye test method comprising exposing the inner surface of the barrier-coated product, or a sample cut out of the product, to a solution containing an intensely colored or fluorescent dye, removing the solution after a given period of time, and examining by visual or instrumental means the degree and depth of dye penetration into the walls of the product. This method is not applicable to products incorporating dark colored and/or opaque pigments and tends to give erroneous results because the diffusion characteristics of low molecular weight, volatile substances may differ greatly from that of the complex organic dyes.

A number of indirect tests are available which include the chemical or physical detection of the active component in the barrier treatment such as fluorine or sulfur from the AIROPAK and Dow Processes, respectively. In addition, the measurement of optical or other physical properties such as contact angle or total reflectance is used. In those cases in which fluorine is used as the active barrier agent, X-ray fluoresence or combustion followed by chemical analysis are applicable. These methods often fail to detect containers with unsuitable barrier properties because a given surface may not be uniformly treated. The optical or physical property measurements have the disadvantage of being highly sensitive to contamination and are difficult to correlate with barrier properties. Finally, all such methods tend to be slow, tedious and relatively expensive to obtain permeation data on containers coming off a production line.

BRIEF SUMMARY OF THE INVENTION

The process of the present invention overcomes the disadvantages of the prior art quality control methods by providing an inexpensive, rapid and accurate measurement of the degree of impermeability of a barrier treated material.

In accordance with the present invention, a process is provided for distinguishing between solid, porous materials having at least one surface treated to impart a measurable degree of impermeability to volatile fluids and an untreated surface which comprises the steps of:
(a) exposing the treated surface to a high concentration of the volatile fluid, either a liquid or gas, for a fixed period of time to allow the fluid to diffuse through the treated surface and into the walls of the solid materials;
(b) removing the excess volatile fluid from the treated surface after the fixed period of time;
(c) exposing the treated surface from step (b) to an environment for causing the fluid to back-diffuse from the walls and through the treated surface into the surrounding atmosphere or environment in which the solid materials are placed; and
(d) measuring the concentration of the fluid back-diffusing into the atmosphere or environment.

The treated surface may be placed in two substantially different environments to achieve the desired purpose. One environment in which the treated materials are placed in an enclosure which is evacuated causing the volatile fluid that has permeated the walls to backdiffuse. The concentration of the volatile substance that is back-diffused can be continuously measured and recorded by means of an electronic vacuum gauge connected to the enclosure.

Alternately, the treated surface is placed in an enclosure, a carrier gas is directed against the surface causing the gas to impinge and the concentration of the volatiles in the carrier gas after impinging is continuously measured and recorded in an analyzer for that particular substance, i.e. a hydrocarbon analyzer in those cases in which the volatile fluid is a hydrocarbon.

The treated material, such as a barrier treated container, is determined to have a high degree of impermeability in comparison to an untreated container if the back-diffusion rate, as measured by the concentration of the solvent back-diffusing from the treated surface into the environment surrounding the container in a short interval of time, is at least one or more orders of magnitude less than the rate of solvent back-diffusing from an untreated surface which has undergone the same steps (a) through (d) set forth above. The fixed period of time for exposing the surface can be as low as 30 seconds and no more than 10 minutes to provide an effective comparison. The length of time for back-diffusion by means of either a vaccum or the flow of carrier gas can be in the same range as this fixed period of time. It is obvious that greater than these times can be used. However, such additional time is believed to be unnecessary to provide a sufficiently good comparison with the untreated substance to determine whether a surface has been treated or not. In the case of determining the degree of permeability of partially treated surfaces, longer periods may be required to establish a valid comparison.

In using a carrier gas, it is essential that the gas be nonreactive with the solvent and the solid material under test. Such a carrier gas can be any inert gas such as nitrogen, argon, helium, xenon, carbon dioxide, neon and the like.

The step of removing the excess solvent from the treated container after the initial exposure involves first removing all free liquid and then purging with a relatively high flow rate of an inert gas to dilute the residual vapor to an insignificant level. A flow rate of several volume changes of gas per minute is adequate. Fourteen total volume changes of the atmosphere dilutes the volatile test substances to less than one millionth of its initial concentration, while 20 changes of the atmosphere reduces the concentration to about two billionths of the initial value. Thus a flow of purged gas providing four or five volume changes per minute for a period of four or five minutes is satisfactory. The flow of inert gas is then lowered to a rate such that a conveniently measurable level of test solvent is present in the exit stream. A flow rate of one or two volume changes per minute has been found satisfactory. A higher or lower rate, which is easily determined by trial, may be employed to produce optimum results in any given application.

BRIEF DESCRIPTION OF THE DRAWING

The drawing is of a series of curves showing the decline of toluene concentration during the back-diffusion time for treated blow molded containers which have been filled with toluene for periods of time ranging from 1 minute to 5 days, which curves are all below the dashed 45° line, in comparison to the much more rapid rate toluene back-diffuses from the untreated containers, which comparison is described in further detail in the Examples Section below.

EXAMPLES

Example 1 A

Tests were performed to determine the permeability of 16 ounce bottles prepared by blow molding high HDPE (0.95 gms./cc.) with air. Air blown bottles have a known toluene weight loss after 28 days at room temperature (23° C.) of 15. wt%. One of the air blown bottles was filled with toluene and allowed to stand for 1 minute. The bottle was then inverted and after the toluene had been poured out, the inverted bottle was flushed with a flow of nitrogen at a rate of about 2800 cc per minute for a period of about 5 minutes. In this period it was concluded that all of the remaining solvent had been removed by evaporation, the bottle was fitted with a two-hole stopper. The stopper contained an inlet tube projecting to a position adjacent the bottom of the bottle and an exit tube that did not project below the bottom of the stopper. The interior surface of the bottle at this point was dry and a flow of nitrogen through the inlet was resumed at a rate of about 850 cc per minute which corresponds to a volume change of about 1.8 volumes per minute. Because of the location of the inlet tube, the nitrogen impinged against the treated interior surface of the air blown bottle and flowed through the exit tube and into a Beckman Model 400 Hydrocarbon Analyzer. The analyzer automatically recorded the hydrocarbon content of the gas which was passed through its hydrogen/oxygen flame by measuring the level of electrically conductive ions in the flame. The resulting record from the analyzer is an arbitrary meter reading which is proportional to the hydrocarbon content of the test gas and may be calibrated by use of known standards. However, for purposes of the present test, calibration was unnecessary and the data as set forth in Table 1 below represents the readings produced directly from the analyzer.

Example 1B

The steps of Example 1A were repeated except the air blown bottle was post-treated with a gaseous mixture of 8% by volume of fluorine and 92% by weight nitrogen for a period of 30 minutes in two separate sequences. In a first sequence, the bottle was charged to a reactor operating at room temperature, purged with nitrogen, evacuated to 30 inches of mercury, vacuum, charged with the fluorine mixture to a pressure of about 3 psig for 15 minutes and the entire sequence was repeated. The interior and exterior surfaces of the bottle were rendered substantially impermeable to hydrocarbons. Specifically the post-treated bottle had a toluene loss after 28 days at room temperature of only about 0.9% by weight.

Examples 2A-5A

The steps of Example 1A were repeated except that the toluene was allowed to soak in separate air blown bottles for periods of 10 minutes, 70 minutes, 24 hours and 5 days for Examples 2, 3, 4 and 5, respectively.

In each of Examples 1 through 5, the readings on the Hydrocarbon Analyzer were begun after the container was dry and the nitrogen flow rate was set at about 850 cc/minute. The readings were taken every minute for the first ten minutes for Examples 1A-5A and were continued at five minute intervals up to 30 minutes for Example 2A and up to 20 minutes for Example 3A.

Examples 2B-5B

The steps of Examples 2A-5A were repeated except that the air blown bottles were post-treated in the same manner as described under Example 1B above and the Hydrocarbon Analyzer was read every minute up to a maximum of 10 minutes for Examples 4B and 5B. Examples 1B, 2B and 3B reached a sufficiently low reading after only 4 or 5 minutes which warranted discontinuing the back-diffusion with a sweep of nitrogen gas. Subsequent studies have shown that for fluorine treated bottles, the maximum amount of time required to reduce the concentration of hydrocarbon being removed from the treated container is about 8 minutes.

Table 1 below presents comparative data for Examples 1-5. All of the data in Table 1 was used in the preparation of the drawing which dramatically illustrates the difference between the high rate of back-diffusion of the solvent in the case of the untreated bottles and the comparatively slow rate of back-diffusion of the toluene from the treated bottles. The 5 curves above the dashed 45° line for the untreated bottles and the 5 curves below the 45° line for the treated bottles of the drawing are shown drawn through just a few representative data points for simplicity sake. However, the 10 curves were based on all of the data of Table 1 without extrapolation.

| | HYDROCARBON ANALYZER READINGS | | | | | | | | | |
|---|---|---|---|---|---|---|---|---|---|---|
| | Example | | | | | | | | | |
| Back-Diffusion | 1 1-Minute Soak | | 2 10-Minute Soak | | 3 70-Minute Soak | | 4 24-Hour Soak | | 5 5-Day Soak | |
| Time | A | B | A | B | A | B | A | B | A | B |
| 0 Min. | 55,000 | 2,700 | 90,000 | 450 | 100,000 | 2,700 | 100,000 | 8,000 | 76,000 | 7,000 |
| 1 Min. | 38,000 | 810 | 70,000 | 240 | 82,500 | 920 | 83,000 | 2,300 | 68,000 | 2,350 |
| 2 Min. | 24,000 | 340 | 54,000 | 170 | 62,000 | 320 | 65,000 | 800 | 61,500 | 900 |
| 3 Min. | 18,000 | 165 | 39,000 | 125 | 52,000 | 140 | 54,000 | 340 | 55,500 | 400 |
| 4 Min. | 12,000 | 110 | 31,000 | 110 | 44,000 | 100 | 47,500 | 190 | 48,500 | 230 |
| 5 Min. | 10,000 | — | 25,500 | 100 | 39,000 | 90 | 44,000 | 150 | 41,500 | 175 |
| 6 Min. | 8,800 | — | 22,000 | — | 37,000 | — | 42,000 | 140 | 36,000 | 150 |
| 7 Min. | 7,200 | — | 19,000 | — | 32,000 | — | 40,000 | 130 | 32,000 | 135 |
| 8 Min. | 5,700 | — | 17,000 | — | 31,000 | — | 38,500 | 120 | 30,000 | 120 |
| 9 Min. | 5,000 | — | 15,000 | — | 28,000 | — | 37,000 | 120 | 27,000 | 115 |
| 10 Min. | 4,800 | — | 13,500 | — | 26,000 | — | 36,000 | 120 | 25,500 | 115 |
| 15 Min. | — | — | 9,300 | — | 20,000 | — | — | — | — | — |
| 20 Min. | — | — | 7,000 | — | 17,000 | — | — | — | — | — |
| 25 Min. | — | — | 5,500 | — | — | — | — | — | — | — |
| 30 Min. | — | — | 4,500 | — | — | — | — | — | — | — |

The data in Table 1 and the drawing illustrate a dramatic difference in the level of toluene vapor that was back-diffused from the treated bottles in comparison to the untreated bottles. The latter exhibited one or more orders of magnitude greater concentration of toluene leaving the bottle's surface at any given time. It is also noted that the slopes of the tangent lines to the curves drawn between Hydrocarbon Analyzer readings for 8, 9 and 10 minutes of back-diffusion time for Examples 4B and 5B, for all intents and purposes, are substantially 0 indicating that it has reached an asymptote in the range of 115–120 analyzer reading. In contrast, the slopes of the tangent lines to the curves through 8, 9 and 10 minutes of back-diffusion time for Examples 1A–5A range from 450 for the bottle which was soaked for only 1 minute in toluene to 2500 for the bottle that was soaked for 70 minutes. It is noted that the untreated bottles of the Examples 3A–5A that had been soaked for a longer period of time exhibit a greater slope between 8 and 10 minutes than the untreated bottles of Examples 1A and 2A that had been soaked in toluene for shorter periods of time. This is contrasted to the slopes of curves for the treated bottles, the data of which confirms that after about 8 minutes, the slopes are independent of the amount of soaking time.

It is believed that the differences between the treated and untreated bottles are the consequence of the much greater amount of toluene which migrates into the untreated bottles during the soaking period and the much greater ease with which the toluene back-diffuses from the walls of the container into the sweep gas. This occurs because of the much greater concentration gradient in the untreated container than in the treated container. It has been shown that the barrier treatment inhibits the diffusion of the toluene into the interior of the treated container and it also inhibits the rate of back-diffusion from the interior of the treated container to the environment surrounding the container during the method of this invention.

The initial high volume purging period for each of the treated and untreated containers to remove the excess toluene varied slightly from one test to another. However, after this short initial purging period, the sweep gas concentrations reflected by the hydrocarbon analyzer readings are distinctly different and directly measure the difference in permeability between the treated and untreated containers.

Example 6

HDPE was extruded through an extruder head maintained at 160°–195° C. to form a parison which was continuously purged with nitrogen, the extruded parison was closed within a mold and a gaseous mixture of 0.7% by volume fluorine and 99.3% by volume nitrogen was injected through a blow pin to expand the parison to conform to the walls of the bottle. The resulting bottle having its interior treated was filled with water, emptied, filled with toluene and allowed to stand for 1 minute. The remaining steps of Examples 1–5 were carried out. The Hydrocarbon Analyzer readings as a function of time are summarized below.

| Back-Diffusion Time, min. | Hydrocarbon Analyzer Readings |
| --- | --- |
| 0 | 1500 |
| 1 | 850 |
| 2 | 590 |
| 3 | 460 |
| 4 | 380 |
| 5 | 320 |

The technical advance of the present process over prior art processes are listed below:
(1) The process can be performed by semi-skilled personnel.
(2) The process requires a very modest investment for equipment.
(3) The process requires only a few minutes to perform for each test.
(4) The process accurately indicates the level of treatment over the entire inner surface of the container.
(5) The process is non-destructive.
(6) The process results in a direct measure of the effectiveness of the treatment.
(7) The process is not significantly affected by extraneous factors such as surface contamination or irregularities.

Although only examples showing the use of the method of the present invention with the permeability of fluorine treated bottles with toluene, it would be within the purview of one having ordinary skill in the art to use this method for testing the barrier properties of bottles treated by the sulfonation and epoxy coating processes and other barrier treatments as well as the testing of other solid materials for organic substances other than hydrocarbons. For example, the process of this invention can be applied to determine the effectiveness of a paint or other protective sealant over a porous surface to the permeation of water or other volatile substances. The measurement of small concentrations of such volatiles in carrier gases is well known. For example, gas chromatography can be used to measure the concentration and actual identification of individual substances for a wide variety of materials. Mass spectroscopy can also be used for measuring low concentrations of such substances.

What is claimed is:
1. A method for distinguishing between a solid material having at least one surface treated to impart a measurable degree of impermeability to a volatile fluid and an untreated material which comprises the steps of:
   (a) exposing the treated surface to a high concentration of said volatile fluid for a fixed period of time,
   (b) removing the excess fluid from said treated surface after said fixed period of time,
   (c) exposing said treated surface from step (b) to an environment for causing volatile fluid to back-diffuse through said treated surface into the environment; and
   (d) measuring if the concentration of said volatile fluid back-diffusing into the environment from said treated surface after a fixed period of time is at least one order of magnitude less than the concentration of such a fluid back-diffusing from said untreated material.
2. The method of claim 1 wherein said treated surface in step (c) is exposed to a vacuum which causes said volatile fluid to back-diffuse.
3. The method of claim 1 wherein said treated surface in step (c) is exposed to a carrier gas which is nonreactive with said volatile fluid and said material and which causes said fluid to back-diffuse and wherein the con- centration of said fluid in said carrier gas is measured in step (d).

4. The method of claim 3 wherein the fixed period of time of step (a) and the fixed period of time for back-diffusing from said treated surface, step (d), are both in the range from about 30 seconds to about 30 minutes.

5. The method of claim 4 wherein said solid material is a thermoplastic container having at least its interior surface treated to impart a substantial degre of impermeability to hydrocarbons.

6. The method of claim 5 wherein step (a) comprises filling said thermoplastic container with said hydrocarbon and wherein step (b) comprises removing the contents of said container and purging said container with an inert gas until its interior surface is dry.

7. The method of claim 3 wherein said carrier gas is an inert gas.

8. The method of claim 7 wherein said inert gas is nitrogen.

9. The method of claim 7 wherein said solid material is a thermoplastic container having at least its interior surface treated with a gaseous mixture of 0.1 to 10% by weight fluorine and 99.9 to 90% by weight inert gas.

10. A method for distinguishing between a barrier treated surface and an untreated surface of solid materials which comprises the steps of:

(a) contacting for a fixed period of time each of the treated and untreated surfaces with a high concentration of a volatile fluid to diffuse through the untreated surface into the interior of said solid material at a more rapid rate than through the treated surface;

(b) ceasing step (a) after said fixed period of time;

(c) contacting each of the surfaces with a high velocity of an inert gas to rapidly dry each of said surfaces;

(d) reducing the velocity of said inert gas and contacting each of said surfaces for a back-diffusion time in the range of about 30 seconds to 30 minutes;

(e) measuring and comparing the concentration of said volatile fluid that back-diffuses into said inert gas after it has contacted each of said surfaces; and (f) distinguishing said treated from said untreated surface which back-diffuses at a greater rate than said treated surfaces.

* * * * *